United States Patent [19]

Benz et al.

[11] Patent Number: 4,561,784

[45] Date of Patent: Dec. 31, 1985

[54] DEVICE AND METHOD FOR FRICTIONALLY TESTING MATERIALS FOR IGNITABILITY

[75] Inventors: Frank J. Benz; Randall C. Shaw; David S. Dixon, all of Las Cruces, N. Mex.

[73] Assignee: The United States of America as represented by the Administrator of the National Aeronautics and Space Administration, Washington, D.C.

[21] Appl. No.: 571,616

[22] Filed: Jan. 17, 1984

[51] Int. Cl.[4] .................................................. G01N 25/00
[52] U.S. Cl. ............................................. 374/8; 73/7;
374/46; 422/78; 436/155
[58] Field of Search .................... 374/45, 46, 50, 8;
73/7; 340/577; 436/155, 160; 422/78

[56] References Cited

U.S. PATENT DOCUMENTS

| | | | |
|---|---|---|---|
| 2,686,211 | 8/1954 | Cargill | 422/78 X |
| 3,033,017 | 5/1962 | Whitehead | 73/7 |
| 3,053,073 | 9/1962 | Baughman | 73/7 |
| 3,221,534 | 12/1965 | Alfred | 73/7 |
| 3,343,399 | 9/1967 | Baker | 73/7 |
| 3,404,557 | 10/1968 | Hecht et al. | 73/7 |
| 3,805,586 | 4/1974 | Dodson et al. | 73/7 |
| 3,834,219 | 9/1974 | Brauer | 73/7 |
| 3,987,661 | 10/1976 | Kamp et al. | 374/8 |
| 4,019,365 | 4/1977 | Woo | 374/46 |
| 4,165,924 | 1/1965 | Wolff | 73/86 X |

FOREIGN PATENT DOCUMENTS

| | | | |
|---|---|---|---|
| 0394736 | 7/1933 | United Kingdom | 436/156 |
| 0864085 | 9/1981 | U.S.S.R. | 374/8 |
| 0885829 | 11/1981 | U.S.S.R. | 374/8 |

Primary Examiner—Daniel M. Yasich
Attorney, Agent, or Firm—Edward K. Fein; John R. Manning; Marvin F. Matthews

[57] ABSTRACT

Test apparatus for determining ignition characteristics of various metal in oxidizer environments simulating operating conditions for materials, the test apparatus has a chamber (6) through which the oxidizing agent flows, and means for mounting a stationary test sample (36) therein, a powered, rotating shaft (E) in the chamber rigidly mounts a second test sample (35). The shaft is axially movable to bring the samples into frictional engagement and heated to the ignition point. Instrumentation 16, 32, 48, 49, 50, 51, 52, 53, 54 connected to the apparatus provides for observation of temperatures, pressures, loads on and speeds of the rotating shaft, and torques whereby components of stressed oxygen systems can be selected which will avoid accidental fires under working conditions.

11 Claims, 4 Drawing Figures

DEVICE AND METHOD FOR FRICTIONALLY TESTING MATERIALS FOR IGNITABILITY

DESCRIPTION

1. Origin

The invention described herein was made in the performance of work under a NASA contract and is subject to the provisions of Section 305 of the National Aeronautics and Space Act of 1958, Public Law 85-568 (72 Stat. 435; 42 U.S.C. 2457).

2. Field of the Invention

This invention relates to test apparatus for ranking or evaluating materials, particularly metals, under operational conditions of various high pressure oxidizer environments in terms of wear characteristics, coefficients of friction, temperatures, etc., bearing on or loading to ignitability of the test material.

3. Background of the Invention

Devices for testing systems and components for response characteristics under particular operating conditions, as torque, r.p.m., environmental gas pressure, friction, temperature, and wear are well known. For instance, Whitehead U.S. Pat. No. 3,033,017 shows a device for identifying steels by sensing the light intensity of sparks created by the abrasive action of a grinding wheel. Baughman U.S. Pat. No. 3,053,073 discloses a bearing material stress tester featuring a pair of oppositely-disposed rollers configured to impart compressive loads on the rotating bearing specimen. Wolff U.S. Pat. No. 3,165,924 discloses a rocket nozzle material tester featuring a combustion chamber in which a propellant is ignited, producing heat and pressure within the chamber in order to evaluate the resistance of a sample material.

Alfred et al U.S. Pat. No. 3,221,534 shows a friction tester featuring a hermetically sealed rotating environmental enclosure in which is supported a weighted member which remains fixed in space under the effect of gravity. One friction member is secured to the inside of the enclosure, and the second friction member is secured to the weighted member such that the two members are in movable friction contact upon rotation of the enclosure.

In Baker U.S. Pat. No. 3,343,399, a rotating ball bearing plate abrades on a specimen. Depth of the circular path worn in the test specimen by the rotating balls is utilized as a measure of the wear qualities of the test material. Dodson et al U.S. Pat. No. 3,805,586 discloses a device for testing cable used to arrest the flight of landing aircraft on an aircraft carrier or the like. The device applies tension and torque load to a specimen cable while a drop weight is used to impart a sudden contact force to the specimen.

Brauer U.S. Pat. No. 3,824,219 shows a tool wear tester in which a steel ball under load is reciprocated across a rotating test sample of metal sheet. Degree of wear on the ball is utilized as a measure of tool wear for the particular sheet metal sample.

However, although metal ignition is a safety hazard of considerable concern in oxygen systems in engineering applications, systems and devices for instantaneously testing materials under operating conditions in stressed oxygen environmental have not been available.

SUMMARY OF THE INVENTION

Consequently, an object of this invention is to provide apparatus for simulating operating conditions of combustible materials in engineering applications, under stressed oxidizer environments, and sensing the various parameters possibly leading to ignition of the test material.

Another object is to provide novel means for protecting the test apparatus from damage due to burning debris from ignited test material.

These objects and others hereafter appearing are attained in the apparatus herein disclosed which includes a body enclosing three aligned body parts separably bolted together and with a central test chamber communicating with the oxygen supply. An appropriately sealed and cooled, powered shaft extends axially through the body and test chamber. Serially located in the test chamber are rotating and stationary test samples secured, respectively, to the shaft for rotation therewith and to the wall of the test chamber. The shaft is axially movable by power means, connected to the shaft through a load cell, for causing frictional engagement between the test samples. Appropriate sensors, e.g. thermoplies, pyrometers, load cells, and tachometers are provided for measurements of static and dynamic phenomena such as frictional force, speeds, temperatures, and pressures. A copper protective sleeve is secured to the test chamber about the test samples.

BRIEF DESCRIPTION OF THE DRAWINGS

In the accompanying drawings.

DESCRIPTION OF THE PREFERRED EMBODIMENTS

Figure 1:
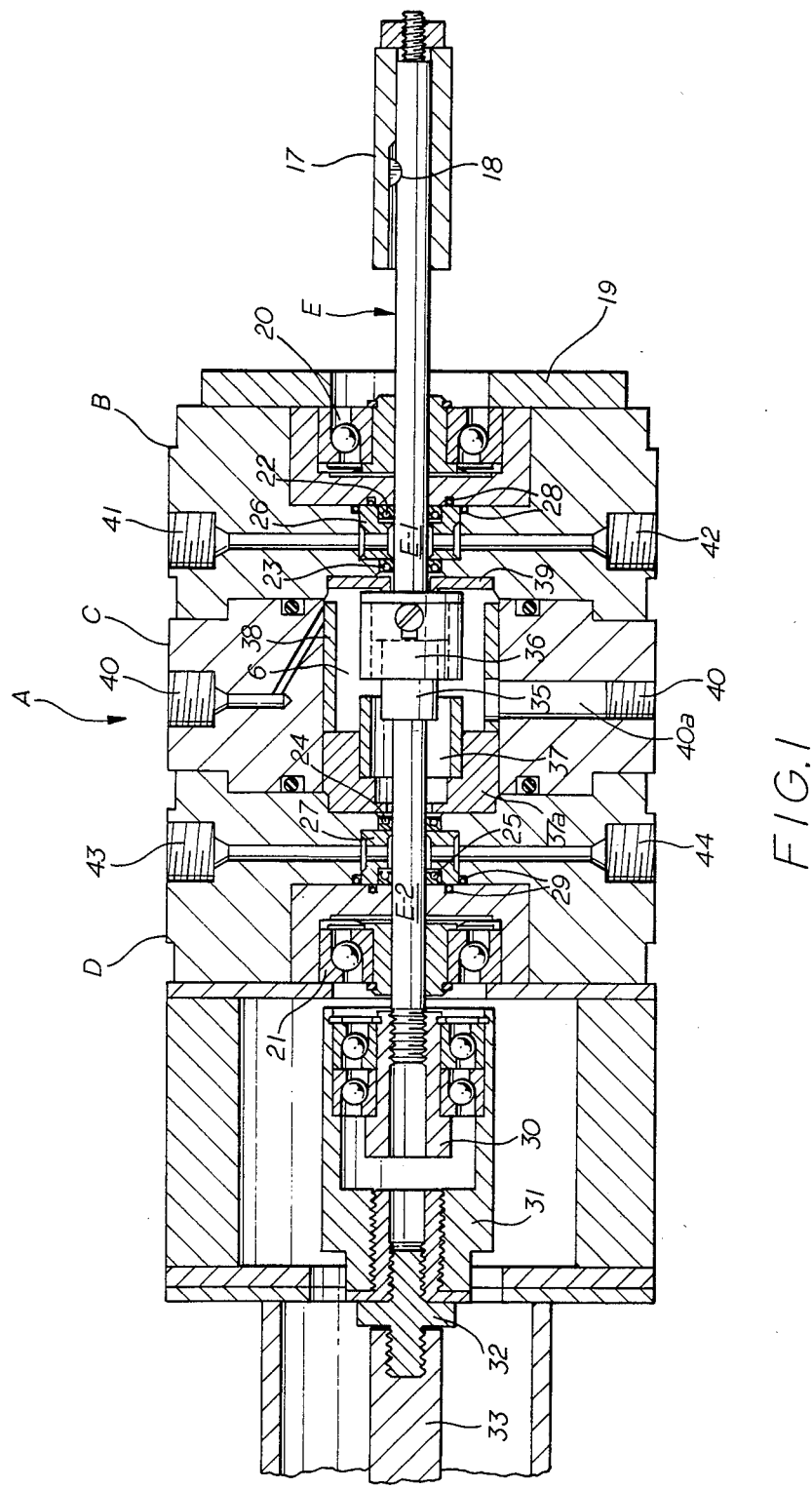
FIG. 1 is a longitudinal cross-section through the test apparatus.
Figure 2:
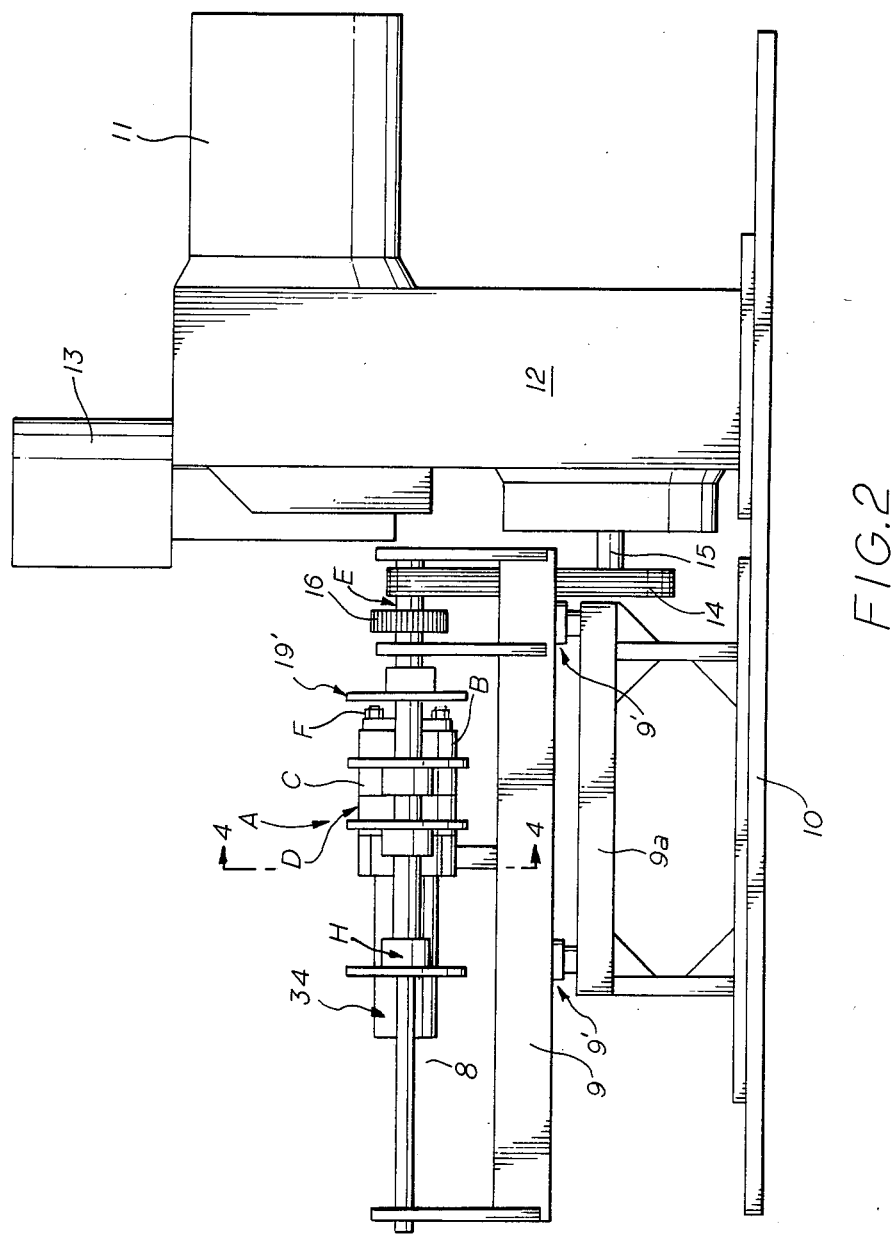
FIG. 2 is a schematic representation of the test apparatus and powering means, parts being omitted for clarity.
Figure 4:
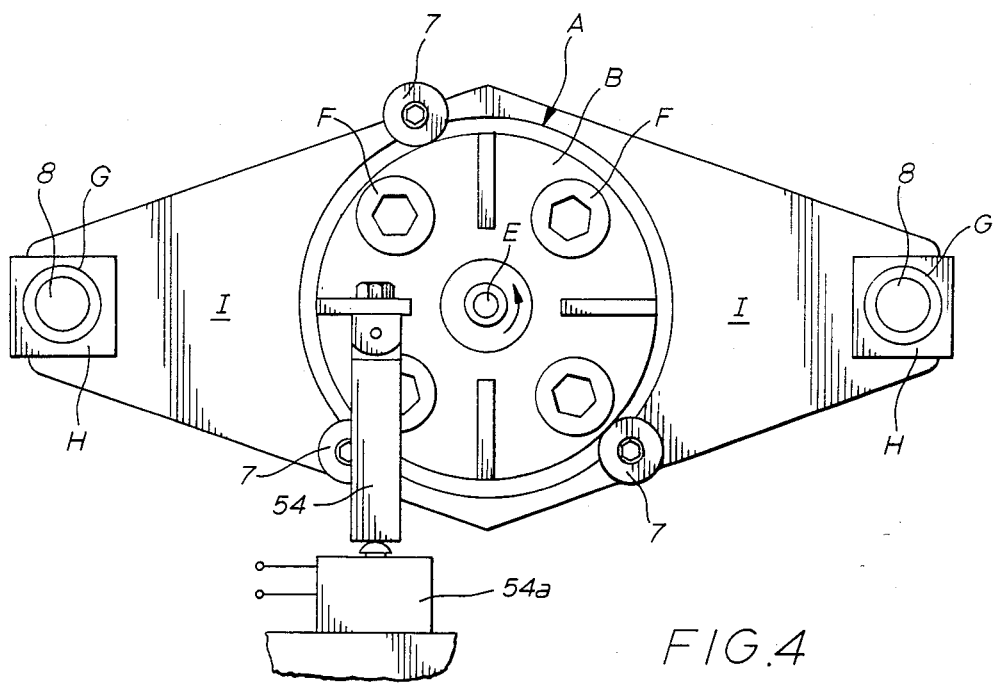
FIG. 4 is a section taken on line 4—4 of FIG. 2.

FIGS. 1 and 4 show the mechanical features of the apparatus including the cylindrical body A with identical end sections B and D and the central section C forming test chamber 6. The body sections are separably secured in alignment by bolts F (FIG. 2 and FIG. 4). The body is rotatably carried in oppositely extending winglike supports I (FIG. 4) through steady rest rollers 7. Supports I are slidable on rails 8 through linear bearings G mounted in pillow blocks H. Rails 8 are carried on an adjustable platform 9, adjustment nuts $9^1$, base $9a$, and flooring 10.

A chamber shaft E extends entirely through the body and has, at its right hand end, powering means including a 15 HP motor 11, a variable pitch belt transmission in a housing 12, a speed control motor 13 and the drive shaft 15. The drive shaft actuates chamber shaft E through a timing belt 14 which drives shaft E (FIG. 2) and a spline 17 (FIG. 1) having a woodruff key 18 which shears at approximately 300 inch/pounds.

A torquing plate $19^1$ (FIG. 2) is suspended between the rails 8. It slides over the flats of plate 19 (FIG. 1) as a backup wrench when the chamber bolts F are being torqued. Shaft E, which in an exemplary embodiment is about 12 inches (30 cm) long, is constructed of PH heated-treated, corrosion resistant steel. Sealing portions E-1 and E-2 of the shaft on opposite sides of the test chamber are polished to 6 microinches (0.00015234 mm) for sealing engagement, respectively, with radial, spring loaded cup seals 22–25 mounted in end-sections B and D, made of molydisulfide, glass-filled Teflon with 17-7 PH springs. These seals are retained by copper fittings 26 and 27, themselves sealed by O-rings 28 and 29. The seals are capable of functioning at peak shaft speeds in an active medium such as oxygen.

Shaft E, at its left hand end, is threadedly secured to the inner member 30 of a thrust bearing assembly 30, 31, the outer member 31 of which is, in turn, threadedly secured through a load cell 32 to the shaft 33 of a pneumatic cylinder 34 for controlled axial shifting of chamber shaft E, for a purpose to be described. A second load cell 54a (FIG. 4) provides a reading of torsional forces on the body A.

A cylindrical test sample holder 35 is pinned and pressed to the center of shaft E within test chamber 6 for receiving the rotating sample 36 rigidly secured thereto. A stationary sample 37 is secured to the test chamber wall in normally spaced relation to the rotating sample by means of holder 37a. A replaceable copper sleeve 38 on the test chamber wall protects the chamber wall and center body member C from burning debris. The chamber end plate 39 shields seals 22, 23 and their fitting 26. Stationary sample holder 37a protects seals 24 and 25 and their fitting 27.

Precision positioning of the shaft through the seals is maintained by deep groove radial bearings 20 and 21 and precision-bored bushings which are pressed into the inner race of the bearings and are close running fits with shaft E.

Oxidizer gas is supplied to test chamber by means of inlet port 40 and exited through port 40a. Cooling agent (water) is circulated through ports 41, 42, 43 and 44 and copper fittings 26 and 27.

INSTRUMENTATION

Figure 3:
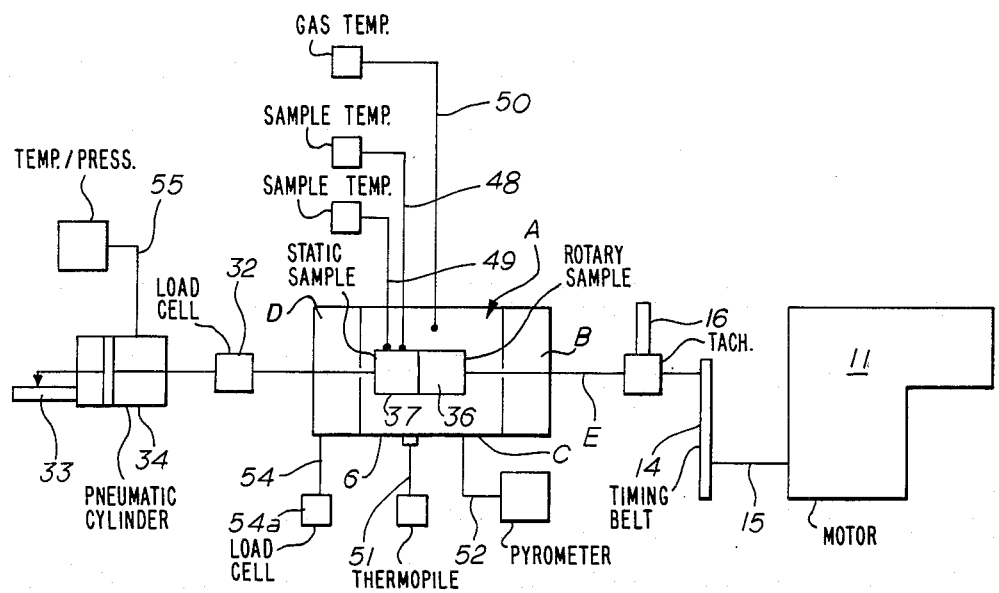
FIG. 3 is a schematic representation of the test apparatus and instrumentation.

Chamber 6 is designed for extensive instrumentation for ready observation and/or recording of the test parameters, as suggested in the block diagram (FIG. 3). Various measuring devices, such as thermoplies 51 and two-color pyrometers 52 may be used where expedient. Test sample and test chamber temperatures are provided at 48, 49, and 50. Tensional loads on chamber shaft E are taken from load cell 32.

Linear displacement of shaft E is dynamically measured by a transducer 53. R.p.m. of shaft E is measured by magnetic pick-up tachometer 16 previously mentioned. Frictional forces and torque are taken from a load cell 54a consisting of a moment arm 54 attached to body A and reacting against rails 8. In addition, the test chamber may be provided with a window for visual or video inspection of test events. Air cylinder temperature and pressure may be read as at 55.

The body is constructed of a nickel copper alloy which makes the apparatus durable in the harsh environment and high temperatures due to the frictionally created high temperature of the burning test samples. The chamber shaft is capable of speeds of 20,000 r.p.m.

In operation, with the test samples as for example, 36 and 37, in place on the respective holders of the shaft E and the test chamber wall, and the oxidizer gas and coolant flowing, shaft E is rotated and shifted axially leftwardly to cause rubbing contact between the opposed ends of the samples. Careful note is made of temperatures, pressures, r.p.m., and loads existing from time to time. The samples are frictionally heated by rubbing contact, if desired, until ignition occurs. Following the test, the three body sections may be unbolted and slid apart to permit removal of burned metal debris and making any repairs necessary preparatory to succeeding test procedures.

Readings from the instrumentation under controlled environments may be utilized to determine and evaluate:

1. Ignition characteristics of the test materials,
2. Materials ranking and selection for various oxidizer services (oxygen, halogens, oxides of nitrogen, etc.)
3. Wear characteristics of material,
4. Coefficient of friction of materials,
5. Data acquired from simulated conditions to aid in design of components and systems.

While original development and successful testing of the invention has taken place in the aerospace program, the invention can simulate operating conditions of any industrial use of metals in a stressed oxidizer environment and is applicable to aircraft and underwater technology and other industrial technologies where high pressure oxygen or halogens are used.

The invention may be modified as will occur to those skilled in the art and exclusive use of all modifications as come within the scope of the appended claims is contemplated.

We claim:

1. A test device for evaluating ignitability of materials under simulated operating conditions in stressed, oxidizer environments comprising a body having a sealable test chamber, a rotationally and axially powered shaft extending axially through said chamber and with seals and bearings in said body on opposite sides of said chamber, means for securing a test sample to said shaft in said chamber for rotation with said shaft, a stationary wear surface of a sample secured to at least a portion of a wall in said chamber, powered means to shift the test sample on said shaft into frictional contact with said surface, means to supply oxidizer to said chamber, means to sense and record friction-powered temperature and ignition of test sample.

2. A test device as described in claim 1 in which said stationary surface is comprised of the material being tested.

3. A test device as described in claim 2 in which said rotatable and stationary test samples are disposed end to end about said shaft for frictional abutment.

4. A test device as described in claim 2 further including a protective sleeve of durable material surrounding the test materials in said chamber.

5. A test device as described in claim 4 in which said sleeve is made of copper.

6. A test device as described in claim 1 further provided with window means in a wall of said chamber for observation of ignition of the test sample.

7. A test apparatus as described in claim 1 further including cooling means for said seals.

8. A test device as described in claim 1 further including load sensing means incorporated with said shaft for determination of normal loads on the material being tested.

9. A test device as described in claim 1 in which said body is constructed of a central chamber part and end shaft bearing parts separably secured together for access to said chamber.

10. The method of evaluating a material for ignitability under simulated operating conditions and due to friction in a stressed, oxidizer environment comprising enclosing a plurality of test samples of like or dissimilar materials on a rotating shaft and a wall of a test chamber each of the samples having frictional contact surfaces in a chamber containing the oxidizer and moving said samples into frictional contact with and relative to said surfaces of each sample under different conditions of stress to cause frictional heating of said samples, and sensing temperature conditions of said samples including ignition thereof.

11. The method described in claim 10 further including sensing frictional loading between said sample surfaces.

* * * * *